United States Patent [19]

Pohl et al.

[11] Patent Number: 4,507,280

[45] Date of Patent: Mar. 26, 1985

[54] HAIR CONDITIONING COMPOSITION AND METHOD FOR USE

[75] Inventors: Stanley Pohl, New Rochelle; Michael Hnatchenko, Bronx, both of N.Y.; Raymond Feinland, Stamford, Conn.

[73] Assignee: Clairol Incorporated, New York, N.Y.

[21] Appl. No.: 348,390

[22] Filed: Feb. 12, 1982

Related U.S. Application Data

[63] Continuation-in-part of Ser. No. 196,716, Oct. 14, 1980, abandoned, which is a continuation-in-part of Ser. No. 080,615, Oct. 1, 1979, abandoned.

[51] Int. Cl.³ .............................. A61K 7/06; A61K 7/09
[52] U.S. Cl. .......................................... 424/70; 8/405; 8/406; 424/71
[58] Field of Search ................................... 424/70

[56] References Cited

U.S. PATENT DOCUMENTS

| | | | |
|---|---|---|---|
| 3,406,238 | 10/1968 | Freyermuth et al. | 424/70 |
| 3,530,215 | 9/1970 | Grief et al. | 424/70 |
| 3,654,936 | 4/1972 | Wajaroff | 424/72 |
| 3,683,939 | 8/1972 | Johnsen | 424/70 |
| 3,715,428 | 2/1973 | Quasius | 424/47 |
| 3,733,312 | 5/1973 | Deetman | 424/47 X |
| 3,760,819 | 9/1973 | Vogt | 424/72 X |
| 3,761,417 | 9/1973 | Parran | 424/70 X |
| 3,876,760 | 4/1975 | Nersesian et al. | 424/70 |
| 3,879,464 | 4/1975 | Kalopissis et al. | 424/70 |
| 3,910,862 | 10/1975 | Barabas | 424/71 |
| 3,912,808 | 10/1975 | Sokol | 424/71 |
| 3,914,403 | 10/1975 | Valan | 424/47 |
| 3,949,087 | 4/1976 | Bacq et al. | 424/70 |
| 3,950,510 | 4/1976 | Adams | 424/DIG. 2 |
| 3,954,960 | 5/1976 | Valan | 424/47 |
| 3,958,581 | 5/1976 | Abegg et al. | 424/70 |
| 3,959,463 | 5/1976 | Nersesian et al. | 424/70 |
| 3,964,500 | 6/1976 | Drakoff | 424/DIG. 2 |
| 3,980,769 | 9/1976 | Ghilardi et al. | 424/70 |
| 3,986,525 | 10/1976 | Sokol | 424/70 X |
| 3,986,825 | 10/1976 | Sokol | 424/DIG. 2 |
| 3,992,336 | 11/1976 | Faucher | 424/70 X |
| 3,996,146 | 12/1976 | Tarason et al. | 424/DIG. 2 |
| 4,001,394 | 1/1977 | Fogel | 424/70 |
| 4,027,008 | 5/1977 | Sokol | 424/62 |
| 4,035,478 | 7/1977 | Mullen | 424/70 |
| 4,038,294 | 7/1977 | Conner et al. | 424/70 X |
| 4,038,995 | 8/1977 | Edelberg | 424/70 |
| 4,061,150 | 12/1977 | Dasher | 424/70 |
| 4,069,347 | 1/1978 | McCarthy | 424/70 X |
| 4,075,131 | 2/1978 | Sterling | 424/70 |
| 4,165,367 | 8/1979 | Chakrabarti | 424/DIG. 2 |
| 4,172,887 | 10/1979 | Vanlerbergh et al. | 424/DIG. 2 |

*Primary Examiner*—Dale R. Ore
*Attorney, Agent, or Firm*—Gabriel P. Katona

[57] ABSTRACT

A hair conditioning composition relatively stable toward repeated shampooings comprising an aqueous acidic composition containing a cationic polymer product, an amphoteric surfactant product and a betaine and a process for treating hair, particularly hair containing an alkaline residue from prior hair treating processes, with the same.

16 Claims, No Drawings

HAIR CONDITIONING COMPOSITION AND METHOD FOR USE

This is a continuation-in-part of U.S. application Ser. No. 196,716, filed Oct. 14, 1980; which is a continuation-in-part of U.S. Ser. No. 080,615, filed on Oct. 1, 1979, both now abandoned.

DESCRIPTION

This invention relates to compositions that are useful in conditioning hair and to processes for conditioning hair that employ such compositions.

It is known in the prior art to treat hair with certain quaternary amine compounds for the purpose of conditioning hair i.e. to improve its combability, manageability, softness, etc. Although such prior art compositions have proven to be effective in varying degrees, one of the chief drawbacks has been the fact that the effect has not been long-lasting i.e. it does not survive repeated shampooings.

It has been disclosed in U.S. patent application Ser. No. 160,151, filed on June 24, 1980 and in any continuing applications based thereon, that hair conditioning compositions can be provided which are relatively stable to repeated shampooings by formulating such compositions so that they consist essentially of an aqueous solution containing a cationic polymer product, an amphoteric surfactant product and sufficient acid to give the aqueous solution a pH in the range of about 1 to 6.

It was disclosed in the aforesaid patent applications that betaines that are amphoteric surfactants do not satisfy the definition of the term "amphoteric surfactant product" and, therefore, cannot be used in compositions of the said patent applications. We have now discovered that by the further addition of certain betaines, the properties of the compositions disclosed and claimed in the aforesaid patent applications, can be very substantially improved.

It is accordingly an object of the present invention to provide an improved hair conditioning composition that is resistant to repeated hair shampooings. It is also an object of the present invention to provide a process for treating hair using the aforesaid composition which has a conditioning effect on the hair that is relatively resistant to repeated shampooings.

Other and more detailed objects of this invention will be apparent from the following description and claims.

The present invention relates to an improved composition for conditioning hair, which includes, based on the total weight of the composition, in an aqueous carrier, from about 0.1% to about 10% of at least one cationic polymer product from about 0.2% to about 20% of an amphoteric surfactant product; and sufficient acid to give the composition a pH in the range from about 1 to about 6; the ratio:

$$\alpha = \left[ \frac{\text{polymer (mer)}}{\text{detergent (mol)}} \right]$$

being from about 0.2 to about 5, including all surfactants in the composition, the improvement comprising the additional inclusion of from about 0.1% to about 5.0% of a betaine of the formula:

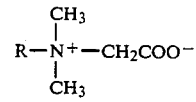

in which R is a long chain aliphatic radical containing 10-24 carbon atoms. The present invention also involves a method for conditioning hair which has been previously treated with an agent having an alkaline pH, by applying thereto the composition of this invention.

Whereas, the betaines in and of themselves in solution do not effect any hair conditioning, in combination with the cationic polymer and amphoteric surfactant, the efficacy of the latter combination as a durable hair conditioning agent is significantly enhanced. Furthermore, the addition of the betaine improves the shelf life of the composition by preventing the formation of two layers upon standing.

The use of a betaine is known, but in a hair shampoo. For example, it is disclosed in U.S. Pat. No. 3,996,146. This patent describes a clear, water-free shampoo formulation which contains a cationic quaternary copolymer of dimethyldiallylammonium chloride and an acrylamide (sold under the trademark MERQUAT 550) and known under its CTFA name as quaternium 40, an anionic detergent as shampoo base and an amphoteric detergent such as a betaine to maintain the cationic polymer in solution and to prevent its interaction with the anionic surfactant in the bottle. Upon the addition of water during shampooing the solvent concentration for the cationic polymer is diluted and the polymer precipitates onto the hair to impart a conditioning effect thereto.

The present invention relates to a durable hair conditioner in an aqueous composition. The conditioning effect remains on the hair throughout repeated shampooings; hence the reference to "durable" conditioning. Therefore the present compositions are not shampoos. Furthermore, the present compositions do not contain anionic surfactants, hence there is no need to prevent an ionic interaction between an anionic surfactant and the cationic resin. In contrast, the aforementioned U.S. Pat. No. 3,996,146 which, by the fact that it relates to a shampoo, does not aim to impart durable conditioning and will, indeed, not do so in view of the fact that its ingredient concentrations are outside of the critical concentration range of the present invention which result in the obtaining of a durable conditioning effect. Furthermore, the present invention does not rely on the addition of water to precipitate the cationic compound onto hair. The aqueous compositions of the present invention are formulated to be especially useful for the durable conditioning of hair which was previously treated with an alkaline medium such as for dyeing or bleaching and, therefore, the thus pre-treated hair carries a residue of the alkaline agent.

The cationic polymers that are useful in accordance with the present invention have at least one positively charged nitrogen or sulfur moiety in each periodically repeating unit. The functional quality of the water insoluble durable conditioning complex that is formed on, and adheres to, the hair, which will resist the effect of several subsequent shampooings, depends on a large extent on the characteristics of the particular cationic polymer that is employed. Therefore, it is conceivable that some of these cationic polymers which have at least one positively charged nitrogen or sulfur moiety in each periodically repeating unit, will not be as effective as others or possibly not effective at all. This, in fact, was observed in the case of a number of cationic polymers.

A simple test was devised to determine the usefulness of materials for the conditioning of hair. The test and the associated simple instrumentation are described in an article by M. Garcia et al. in 27 Jnal. Soc. Cosmetic Chemists pp. 379–398 (Sept. 1976) entitled "Combability Measurements on Human Hair", which is incorporated herein by reference thereto. The conditioning of hair is defined for purposes of the present invention as increasing the ease by wich a comb can be pulled through freshly washed hair. The term "durable conditioning" as is used throughout the specification and the claims means that after the application of the conditioning composition and the employment of a durable conditioning process, hair is easier to comb after at least three subsequent shampooings, than it is to comb when no conditioning was employed, even after a single shampoo. This defines what is meant by "durable" when we refer to "durable conditioning".

Whether hair is effectively conditioned or not can be simply determined by employing the measurement described in the abovementioned article on combability measurements. A hair swatch is suspended from an Instron Tensile Tester having a load cell B which has a range of 0–2000 g. Other recording tensile testing instruments can also be used. An attachment is provided having a comb stand, a comb, clamps and the like. The exact character of the measuring device is not critical, since always relative values are determined in comparison to untreated hair. For determining the base line control value for a given hair, the hair swatch is soaked in water, then is combed out until detangled. Then the hair is dipped into water several times to cause controlled tangling. The the hair is combed out and the force required to move the comb down through the hair swatch at constant speed is recorded. The effect of treatment on the hair swatch is determined by treating the swatch with an amount of treating agent, in the same manner as treatment is intended to be given to hair in actual use. The hair swatch is then relaxed by a 5 minute immersion in water and again the force is measured that is required to pull a comb through the swatch at constant speed. The difference is then calculated and will provide a measure of the conditioning efficacy of the treatment. In the case of the present invention the treatment is followed by 3 subsequent shampooings and, therefore, the measurement not only provides information about the conditioning efficacy of the treatment, but also about the durability of the effect.

In the case of the present invention in defining whether we can consider hair to have been conditioned, we cannot employ a scale of absolute force values as could be measured in accordance with the aforementioned article. This is because there are many different kinds of hair, all of which have different combability characteristics. Therefore, it is not unusual that one variety of hair requires a force tenfold or more than the force required to comb another variety of hair that is in a stage of identical conditioning. Notwithstanding this fact, conditioners have been found generally, and especially in the case of the present invention, to improve the combability of all given varieties of hair that were tested.

Accordingly, we have assigned a subjective scale of 5 values to define the ease of combing, i.e. the degree of conditioning of hair, with the value 1 representing the combability of hair that was not conditioned at all. The value 2 represents a slightly perceptible increase in the ease of combing, but we do not consider hair to have been conditioned until it has a value of at least 3. If hair has a value of 3 after 3 shampooings, then we consider it to have been durably conditioned. It should be kept in mind that these five subjective ease-of-combing values are relative ones and are comparable to each other only when used in each case on the same kind of hair.

On the arbitrary scale of 5 values, the value 1 was assigned to wet, untreated hair and 5 to the best durably conditioned value. In accordance with the force measurement that is required for combing, as described above, a maximum conditioning at level 5 would require about 1/10 of the force that is required for an untreated swatch of wet hair. If we consider a level 5 as representing a conditioning improvement of approximately 100%, then we can assign to levels 2, 3 and 4 a very approximate improvement of 25%, 50% and 75%, respectively.

As used throughout the specification and the claims, the term "cationic polymer product" denotes a cationic polymer containing a quaternary moiety which is at least one positively charged nitrogen or sulfur moiety in each periodically repeating until and which can form a substantially water insoluble complex when contacted with an ionic surfactant in the presence of hair, said complex durably conditioning the hair.

A number of different cationic polymers were tested to determine whether they satisfy the aforementioned requirements of a cationic polymer product. As a result of such testing it was determined that it is entirely unpredictable from the structural characteristics of a polymer whether or not it will perform as a cationic polymer product. For example, while quaternium-40, a dimethyldiallylammonium chloride homopolymer sold by Merck & Co., Inc. under the name Merquat-100, performed satisfactorily under the criteria for durable conditioning, as described above and is, therefore, a cationic polymer product, but its low molecular weight (5000) homolog is not, although even a lower molecular weight (3000) cationic polymer (polyquaternium-1) performed satisfactorily.

Other examples of cationic polymers which are not cationic polymer products because they did not perform satisfactorily are given by their official CTFA (Cosmetic, Toiletry and Fragrance Association) names, where available, as contained in the CTFA Cosmetic Ingredient Dictionary (1977 edition), followed by their trademark and source in parentheses. These are:

adipic acid/epoxypropyl diethylenetriamine copolymer (sold by Hercules Chemical C0. under the name Delsette 101);

adipic acid/dimethylaminohydroxypropyldiethylenetriamine copolymer (sold by Sandoz, Inc. under the name Cartaretin F-4);

poly [N-(3-dimethylamino)propyl]-N'-[3-(ethyleneoxyethylene dimethylamino)propyl] urea dichloride (sold under the name Mirapol A15 by Miranol Chemical Co., Inc.);

quaternium-23, a quaternary ammonium polymer formed by the reaction of dimethyl sulfate and a copolymer of vinyl pyrrolidone and dimethylaminoethylmethacrylate (sold by GAF Corporation under the name Gafquat 755N);

quaternium-19, a polymer of hydroxyethyl cellulose reacted with epichlorohydrin and then quaternized with trimethylamine (sold by Union Carbide Corp. under the name Polymer JR-400);

a quaternary ammonium derivative of a hydrolyzed collagen protein (sold by Croda, Inc. under the name of Crotein Q);

quaternium-39, a copolymer of acrylamide and beta-methacryloxyethyl trimethyl ammonium methosulfate (sold by Hercules Chemical Co. under the name Reten 205M);

aminoethylacrylate phosphate/acrylate copolymer (sold by National Starch Co. under the name Catrex); and quaternium-41 which is a copolymer of dimethyldiallylammonium chloride with acrylamide (sold by Merck & Co., Inc. under the name Merquat-550).

quaternized poly-2-vinylpyridine.

On the other hand, a number of other cationic polymers were found to perform well as ingredients of durable conditioning compositions in accordance with the present invention and they satisfy the definition of a cationic polymer product.

The cationic polymer products that were found so far are:

quaternium-40, already mentioned above as one good example. It is said to be constituted of repeated units of the moiety:

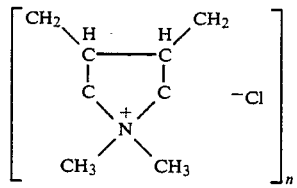

where n is a cardinal number proportional to the molecular weight of the polymer.

Other cationic polymers that were so far found to be cationic polymer products, are:

polyquaternium-1, a polymeric quaternized dimethylbutenylammonium chloride terminated with quaternized triethanolamine groups, sold by Onyx Chemical Co. under the name Onamer M, hereinafter referred to as "Onamer", and said to have the formula:

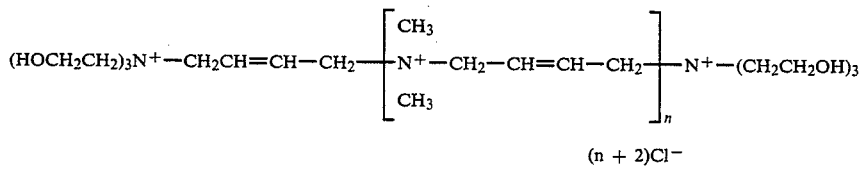

(n + 2)Cl⁻ where n is a cardinal number which is proportional to molecular weight;

quaternized poly-4-vinyl pyridine, hereinafter referred to as "QPVP", which is believed to be constituted of repeated units of moiety:

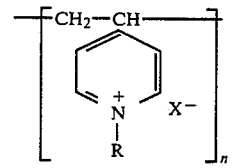

where n is a cardinal number which is proportional to molecular weight, R is a $C_1$–$C_{20}$ alkyl radical and X is a cosmetically acceptable anion such as a halide, sulfate or carboxylate, which can be made by quaternizing and then polymerizing vinylpyridine in a manner known per se;

poly(methacrylamidopropyltrimethylammonium chloride), hereinafter referred to as "Clairquat-1", which is made by polymerizing in a manner known per se the corresponding monomer sold by Texaco Chemicals under the name MAPTAC and which polymer is said to be constituted of repeating units of the moiety:

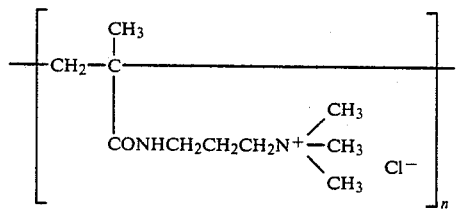

where n is a number which is proportional to molecular weight;

quaternized poly(vinylamine), hereinafter referred to as "QPVAMINE", which can be made by quaternizing and polymerizing vinylamine in a manner known per se, and which is believed to be constituted from repeating units of the moiety:

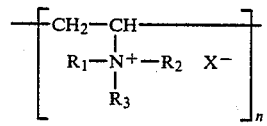

in which $R_1$, $R_2$, and $R_3$ are the same or different and represent $C_1$–$C_{20}$ alkyl groups, and X is a cosmetically acceptable anion such as a halide, sulfate, or carboxylate; and quaternized poly(ethyleneimine), hereinafter referred to as "QPEMINE", which can be prepared by quaternizing and polymerizing ethyleneimine in a manner known per se, and which is believed to be constituted from n repeating units of the monomeric moiety:

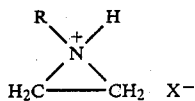

where n is a cardinal number which is proportional to the molecular weight of the polymer, R is a $C_1$-$C_{20}$ alkyl group, and X is a cosmetically acceptable anion such as a halide, sulfate or carboxylate.

In many of the foregoing cationic polymers quaternization can be carried out subsequent to polymerization in a manner known per se.

In the foregoing enumeration of specific cationic polymers, whether or not they also are cationic polymer products, the chemical structures are those that were given by the respective manufacturers or were otherwise postulated. Therefore the formulae dot not necessarily accurately represent the actual structures of the respective monomeric units that constitute the particular cationic polymer. For example, it was recently learned that the manufacturers of two of the cationic polymer products in the foregoing listing changed their views about the formulae which they initially provided for their respective cationic polymers without changing their respective products. The new structural representations, as provided by their respective manufacturers, appear in this application with respect to those two cationic polymer products. It is for that reason that we do not wish to be bound to any specific structural representation of any cationic polymer product herein, but in each case view the manufacturer's trademark, the CTFA designation and any chemical name (the latter usually based on what was done to a precursor to obtain the end product), to be of equal significance in defining each cationic polymer product.

All of the aforementioned cationic polymer products, which by definition of that term will work in accordance with the present invention, were determined to have a value between 3 and 5 on the comb ability test described above and conducted after 3 shampooings subsequent to the application of the composition. Thus their ability has been established to impart durable conditioning properties to compositions and to hair treated thereby.

Since it has been demonstrated that the functioning of the cationic polymer in accordance with the durable conditioning features of the present invention cannot be predicted, and since it has also been demonstrated how the suitability of a polymer within the aboveidentified group can be established by simple routine experimentation, therefore, the term "cationic polymer product", as used throughout the specification and the claims, includes all cationic polymers of the type defined above. Thus the term "cationic polymer product", as used throughout the specification and the claims, includes in its definition not only cationic polymers which have been specifically enumerated herein, but also any and all other cationic polymers which are a "cationic polymer product", as defined hereinabove, as the present invention does not reside in the identity of any given cationic polymer product, nor does it reside only in the employment of any given cationic polymer product, but in the manner that any cationic polymer product is employed.

As it can be readily appreciated, the term "cationic polymer product" is not restricted to homopolymers, but copolymers of multiple monomers are intended to be included in the meaning of the term.

Those specific cationic polymers that were enumerated above as being cationic polymer products, were found to perform, with one exception over a wide range of molecular weights between about 4,000 to about 550,000; most of them suitably from about 20,000 to about 100,000. The only exception that was found so far is Onamer which provides an effective cationic polymer product at a molecular weight between about 1,000 and about 3,000. The manner of determining and expressing the molecular weight makes no difference in this case.

The term "cationic polymer product" as used throughout the specification and the claims also includes mixtures of one or more cationic polymer products. As employed in accordance with the present invention cationic polymer product was found to be sufficient to be present in the composition in concentration between about 0.1% to about 10%, suitable from about 1% to about 5%.

The mechanism of the durable conditioning reaction obtained in accordance with the present invention is not clearly understood. We believe that initially the positively charged sites of the cationic polymer product component of the composition forms a bond with the negatively charged sites of the hair. Up to this point the assumed mechanism is similar to the known, normal conditioning of hair when positively charged monomeric or polymeric quaternary amines are employed for conditioning. While we postulate that, in accordance with our invention, the remaining free positive charges of the cationic polymer product react in the presence of hair with the anionic surfactant to form the durable conditioning complex on the hair which remains attached to the hair and conditions it through several shampoos without need for reapplication each time, we do not wish to be bound by this speculative assertion.

It was found, surprisingly, that in most cases durable conditioning could be obtained at most pH levels. Hair is built of amino acids. These are basic molecular units which contain both positive and anionic charges. When the final polymeric character of the hair is established, there is generally believed to be an equal number of the negative and positive charges present in the hair. Thus hair can be termed to be an amphoteric bipolymer. The neutrality of that system, which means that there is a region of pH at which the number of positive charges and the number of negative charges are equal, is called an isoelectric region. That isoelectric region in hair is approximately pH 4. Above pH 4, on the basis of the charges present in the hair, any agent, such as moistening the hair, should render the hair negatively charged. An agent at a pH below 4 should render the hair positively charged. While this is a theoretical dividing line in practice we find that, possibly due to the wearing properties of the hair, the surface characteristics of hair do not mirror our chemical calculations, which means that the head is able to pick up cationic materials at a pH even lower than 4. It could only pick up cationic materials if the hair surface was negatively charged; that probably can extend down to about pH 2. We can measure this activity of the cationic material by treating the hair with radioactively tagged cationic surfactants and measure the radioactivity of hair. When this is done it is found that hair has approximately no charge in terms of its surface activity or surface affinity, at about pH 2. Any cationic polymer product above pH 2 is likely to be attached to hair, although more of the surfactants are expected subsequently to be bound at pH 7 than at pH 4.

The quantity of cationic polymer product contained in the present aqueous solutions will depend on the particular results that are desired. Ordinarily, this will constitute between about 0.4% to about 10% by weight based on the total weight of the aqueous composition with the optimal range being between about 1% to about 5% on the same weight basis.

The second essential component of the compositions of this invention are the amphoteric detergents. A characteristic of these materials is that many assume the character of an anionic or a cationic surfactant compound depending upon the pH of the solution in which it may be contained. There are a number of amphoteric detergents that are suitable for use in the present invention and we expect that most of the surfactant detergents will work here. We have found that at least elevent different betaines, which are normally classified as amphoteric surfactants, will not form a conditioning complex with a cationic polymer product, even at an alkaline pH level at which the betaine is a cationic surfactant. Betains are rather unique zwitterionic compounds, therefore, we assume that all betaines, and possibly other, similar amphoteric surfactants, such as hydroxy sultanes, possibly even some other zwitterionic surfactants such as those based on amino acids, cannot be employed as amphoteric surfactants in accordance with the present invention. However, we tested at least one zwitterionic amphoteric surfactant the 1977 CTFA name of which is sodium lauriminodipropionate (sold under the trade name DERIPHAT-160C by General Mills Corp.) and this surfactant could be employed as an amphoteric surfactant in accordance with the present invention.

It is a surprising feature of the present invention that even though betaines cannot be used as the amphoteric surfactant in the compositions of the aforesaid application Ser. No. 160,151, when betaines are incorporated into these compositions, the properties of the compositions and the durable conditioning results are considerably improved. Accordingly, we found that by the addition of betaines the aforementioned arbitrary scale of 5 values could be extended to 6 or even 7.

Since there is some question, at least in the case of some amphoteric surfactants, whether they can be employed in the compositions of the present invention, we intend to denote by the term "amphoteric surfactant product" all amphoteric surfactants which, in accordance with the present invention, will form a water-insoluble, durable conditioner precipitate in the presence of hair. This, of course, can be easily determined by routine exprementation, e.g. by means of the test that is also employed to determine whether a cationic polymer is a cationic polymer product, as defined herein. In carrying out a test to determine whether an amphoteric surfactant is an amphoteric surfactant product, it is clear that a cationic polymer has to be employed that is a cationic polymer product, otherwise the results would not be meaningful. The same applies to the use of a known amphoteric surfactant product when determining whether a cationic polymer is a cationic polymer product.

We found that there is a most easy and fast preliminary method by which one can prescreen compounds whether they are candidates for further testing to determine whether a candidate is a cationic polymer product as an amphoteric surfactant product. Accordingly in the case of checking out an amphoteric surfactant, the amphoteric compound to be screened is introduced into a test tube containing a composition having a pH above the pKa value of the amphoteric surfactant and containing an aqueous solution of a known cationic polymer product. If a water-insoluble precipitate is formed then the composition is further tested on a hair tress to determine whether conditioning and durable conditioning can also be achieved. So far the cationic polymers and amphoteric surfactants which we tested were found not to be cationic polymer products and amphoteric surfactant products, respectively, unless they formed a water insoluble precipitate during prescreening in the test tube, according to the aforementioned procedure.

Therefore, it can be appreciated that compounds that are cationic polymer products and amphoteric surfactant products can be readily and easily identified in the future.

In view of the disclosure of the present invention materials can be easily and simply screened to determine their suitability as cationic polymer products and amphoteric surfactant products, respectively. Accordingly, all of such materials, whether or not specifically referred to in this application, are to be regarded as being a part of our invention.

Two classes of amphoteric detergents have been found to be particularly effective. The first class can be defined by the formula:

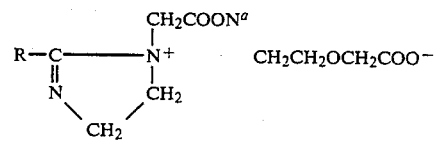

in which R is a long chain fatty radical containing from 10 to 18 carbon atoms. A typical example of such a compound or compounds is the case in which R represents coconut fatty radicals. A material of this character is sold under the trade name MIRANOL C2MSF and is described in the CTFA Cosmetic Ingredient Dictionary (1973) under the name amphoteric-2.

A second class of amphoteric detergents that is particularly effective of the purposes of the present invention can be defined by the formula:

wherein R is a long chain fatty alkyl group having from 10 to 18 carbon atoms. An example of such a detergent is marketed under the trade name DERIPHAT 170C in which the R in formula IV is a mixture of lauryl and myristyl fatty alkyl groups. This material is described in the CTFA Cosmetic Ingredient Dictionary (1973) as lauraminopropionic acid.

The quantity of amphoteric detergent which will be contained in the composition of this invention will vary somewhat, again depending on the economics and the results sought. However, usually this will be in the range of from about 0.2 to about 20% by weight and ideally in the range of from about 1% to about 5% by weight based on the total weight of the composition.

The role of the correct pH for the composition is important substantially to prevent the formation of the insoluble precipitate before the composition of the present invention comes into contact with the hair. Normally at the pKa value of an amphoteric surfactant the anionic and the cationic versions of the surfactant are in equilibrium. One would expect that the use of pH level at this pKa value would, therefore, bring about an ionic interaction between the cationic polymer and the anionic part of the amphoteric surfactant product. This is however, not the case in all situations, because we found that in some cases a pH level above the pKa value of the amphoteric can be used and the composition of the present invention still remains clear because no precipitate is formed. This may be because the compatibility of the amphoteric and cationic ingredients (i.e. the lack of precipitation) may not only depend on the nature of the changes of the materials, but also any possible effect that any side chains on the ingredients may have in the reaction and on the solubilization characteristics of the reaction product. Therefore, the pH of the composition is given as being between 1 and 6, but the composition should be maintained at a pH level between these limits, at a pH at which it remains essentially clear and no substantial amount of precipitate is formed.

Any of a variety of acids may be used in adjusting the pH of these compositions to the proper level, hydrochloric, citric, and phosphoric acids were found to be particularly useful and suitable.

Although the cationic polymer products and the atmospheric surfactant products and any pH-adjusting acid and a betaine of the specified type are the essential active ingredients in the present compositions, the compositions contemplated by the present invention may also contain other ingredients which may serve to improve the organoleptic character of the product or its ease of application. Thus, it is within the purview of this invention to incorporate in the present compositions such materials as fragrances, thickening agents, fragrance solubilizers, solvents, bactericides, etc.

Aside from the absolute quantities of the cationic polymer product and amphoteric detergent contained in the present compositions, it has been found that their conditioning effectiveness is highly dependent upon the "molar ratio" of polymer to detergent. The term "molar ratio" as used herein is designated by the letter α and is defined as:

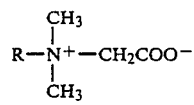

where the term [polymer (mer)] refers to the number of mols of the repeating units of the polymer contained in the composition and bearing a positive charge. The term [detergent (mol)] in the aforesaid expression and elsewhere is defined as the number of mols of surfactant contained in the composition. The ratio may vary somewhat. Ordinarily, this will be in the range of from about 0.2 to about 5 and preferably in the range of from about 1 to about 2.

The betaines that are useful for the purposes of the present invention may be described by the formula:

$$R-\underset{\underset{CH_3}{|}}{\overset{\overset{CH_3}{|}}{N^+}}-CH_2COO^-$$

in which R is a long chain aliphatic radical containing 10 to 24 carbon atoms. As used herein, the term long chain aliphatic radical includes saturated and unsaturated straight chain and branch chain radicals, hydrocarbon radicals as well as chain radicals that include other atoms in addition to carbon atoms in the chain (e.g. oxygen, nitrogen, etc.).

By way of illustrating typical betaines that may be used in this invention, mention may be made of cocamidopropyl betaine, oleyl betaine, cetyl betaine, coco betaine, etc. Cocamidopropyl betaine is described by the formula:

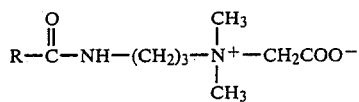

wherein

is the coco fatty acid acyl radical. Coco fatty acid is a mixture of fatty acids obtained from coconut oil which are predominantly $C_{12}$ acids. Oleyl betaine, on the other hand, may be described by the formula:

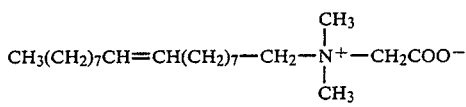

Structurally the coco betaine and cetyl betaine resemble the oleyl betaine shown in the formula above except that the oleyl radical is replaced with coco fatty radicals or the cetyl radical respectively. A number of betaines useful for the purposes of the present invention are available commercially. Among these mention can be made of the following betaines referred to by their CTFA adopted names: cocamidopropyl betaine (solde under the trademark Chemadene NA30 by The Richardson Co., coco betaine, lauryl betaine and cetyl betaine (all sold by Lonza, Inc. under the respective trademarks Lonzaine 12C, Lonzaine 14C and Lonzaine 16S).

The quantity of the betaine that can be incorporated in the compositions of the present invention may vary. Usually, it will comprise between about 0.1% to about 5% by weight and preferably between about 0.3% to about 3% by weight based on the total weight of the composition.

A variety of solvents can be employed in the compositions of the present invention. These will usually take the form of an aliphatic alcohol or ether, either a monohydric or polyhydric, preferably having from 1 to 6 carbon atoms. As employed herein, the term "aliphatic alcohol" is used in its generic sense and includes such alcohols as straight chain and branched chain alkyl alcohols that can be monohydric or polyhydric (e.g. dihydroxy) either alcohols, ester alcohols, etc. By way of illustrating the solvents that may be useful for the present compositions, mention may be made of ethanol, carbitol, hexylene glycol, propylene glycol. The solvents may be used at levels from 0% to about 50% and preferably in the range of from 0% to 5% by weight based on the total weight of the composition.

To facilitate the application of the present compositions to the hair it is often useful to increase their viscosity. Many thickening agents can be used for this purpose. Among these mention may be made of hydroxyethyl cellulose, carboxymethyl cellulose, the Carbopols, e.g. Carbopol 940. However, hydroxyethyl cellulose has been found to be particularly suitable. The concentration of the thickening agent may vary somewhat depending on the results desired. Usually, this will be present in the range of from 0% to about 10% by weight based on the total weight of the composition.

It is often useful to incorporate a bactericide in the compositions of this invention. A variety of materials are known in the prior art that will serve this purpose. By way of illustration, mention may be made of quaternium-15, sold under the trade name Dowicil 200. The quantity of bactericide that will be contained in the present compositions will vary somewhat depending on the nature of the particular composition. Usually, however, it will comprise between 0% to about 10% by weight based on the total weight of the composition.

The compositions of this invention can be applied to hair in any suitable manner. One typical procedure involves applying the conditioning composition, such as described in the examples below, to freshly dyed or bleached hair, working it gently into the hair mass, leaving the composition on the hair for one to three minutes and rinsing the hair thoroughly with water prior to combing and drying. The amount of the conditioning composition applied to hair may vary but, in general, should not be less than 1% of the hair weight and does not need to exceed 20% of hair weight.

It is envisioned that the compositions of this invention will be applied to hair that has previously been given a treatment that leaves the hair somewhat alkaline. Typical of such treatments are those with oxidation hair dye systems or bleaching systems. One such treatment involves mixing a dye base containing, among other things, the oxidation dye intermediates with an aqueous vehicle containing an oxidizing agent such as hydrogen peroxide and then working this mixture into the hair. These mixtures before being applied to the hair usually have an alkaline pH e.g. in the range of from 7 to 12 and preferably 8 to 11. Another such treatment involves for example treating the hair with an alkaline bleaching solution which contains the usual oxidizing agent (e.g. aqueous hydrogen peroxide), boosters (e.g. potassium persulfate and ammonium persulfate), alkalizing agents, etc.

When the compositons of this invention are applied to hair that has been previously treated as indicated above and then rinsed, the combination of amphoteric detergent and cationic polymer precipitates out on the hair due to the action of the residual alkalinity, forming a water insoluble conditioning complex that attaches to the hair and, as indicated, is highly resistant to repeated shampooings.

The pH of the hair conditioning compositions that are employed in the present invention will be selected to some extent on the basis of the alkalinity of the hair to be treated and the relative amounts of cationic polymer products and amphoteric detergent. In general, the pH is selected so that after the composition is applied to the hair and comes under the influence of the residual alkalinity of the hair that the pH of the composition is increased by approximately 1 pH unit above which the precipitation of the complex takes place. Generally the optimum precipitation of the conditioning complex appears to take place under these conditions.

It is our belief that the over-conditioning of hair or the depositing on, and bonding to, hair of excessive amounts of the conditioning complex, i.e. a buildup, is avoided in the use of the present invention. We believe that this is because the number of negative charges on hair, which can accept a conditioning deposit, is proportional to the need and locations on the hair that require conditioning. Since it is believed that the bonding of conditioning complex precipitated according to the present invention takes place between the negative charges on wet hair and the positive charges of the complex precipitate, we would expect that any excess of surfactant, cationic polymer product or complex formed by them, would rinse away rather than deposit onto and overcondition the hair.

The following examples are given further to illustrate the present invention. It is to be understood, however, that the invention is not limited thereto. CTFA names are used in the examples, where possible.

EXAMPLE 1

| Ingredient | % by Wt. |
|---|---|
| quaternium-40 | 3.50 |
| amphoteric-2 | 1.75 |
| hydroxyethyl cellulose | 2.00 |
| phosphoric acid | 0.07 |
| ethanol | 4.00 |
| sodium hydroxide | 0.01 |
| cocamidopropyl betaine | 2.00 |
| water QS to | 100.00 |
| pH 4.5 | |

The use of this composition produces a durable conditioning rating of 5 on the aforementioned arbitrary scale.

EXAMPLE 5

Same as Example 1 except that 2.00% oleyl betaine is used in place of the cocamidopropyl betaine used in Example 1. This composition had a pH of 4.5

EXAMPLE 3

| Ingredient | % by Wt. |
|---|---|
| poly-4-vinyl methyl pyridiniuym iodide (QPVP) | 2.00 |
| amphoteric-2 | 4.00 |
| lauryl betaine | 1.50 |
| hydroxyethyl cellulose | 2.00 |
| phosphoric acid | 1.60 |
| fragrance | 0.10 |
| water QS to | 100.00 |
| pH 4.5 | |

EXAMPLE 4

| Ingredient | % by Wt. |
|---|---|
| poly-4-vinyl lauryl pyridiniuym sulfate (QPVP) | 1.00 |
| cetyl betaine | 1.00 |
| amphoteric-2 | 4.00 |
| hydroxyethyl cellulose | 2.00 |
| phosphoric acid | 1.60 |
| fragrance | 0.10 |
| water QS to | 100.00 |
| pH 4.5 | |

| Ingredient | % by Wt. | | |
|---|---|---|---|
| | Ex. 5 | Ex. 6 | Ex. 7 |
| quaternium-40 | 5.00 | → | → |
| hydroxyethyl cellulose | 2.250 | → | → |
| phosphoric acid | 0.450 | → | → |
| sodium hydroxide | 0.015 | → | → |
| amphoteric-2 | 2.560 | → | → |
| sorbic acid | 0.100 | → | → |
| quaternium-15 | 0.100 | → | → |
| carbitol | 3.00 | → | → |
| cocamidopropyl betaine | 0.600 | → | → |
| fragrance | 0.400 | → | → |
| polysorbate-20 | — | .001 | — |
| polyoxyethylene (20) isohexadecyl ether | — | — | .001 |
| water to 100% | → | → | → |
| pH | 4.8 | 4.5 | 4.5 |

| | Ex. 8 | Ex. 9 | Ex. 10 | Ex. 11 | Ex. 12 | Ex. 13 |
|---|---|---|---|---|---|---|
| quaternium-40 | 5.0 | — | — | 5.0 | 5.0 | 5.0 |
| hydroxyethylcellulose | 2.25 | → | → | → | → | → |
| sodium hydroxide | 0.15 | → | → | → | → | → |
| phosphoric acid | 0.2 | 0.46 | → | → | → | → |
| lauraminopropionic acid | 2.0 | → | → | → | → | → |
| amphoteric-2 | — | 2.56 | → | → | → | → |
| sorbic acid | 0.1 | 0.1 | → | → | → | → |
| quaternium-15 | .1 | 0.1 | → | → | → | → |
| carbitol | 3.0 | → | → | → | → | → |
| fragrance | 0.40 | → | → | → | → | → |
| cocamidopropyl betaine | 2.0 | 2.0 | 2.0 | — | — | — |
| quaternium-40 | — | — | 12.5 | — | — | — |
| Onamer | — | 5.0 | — | — | — | — |
| coco betaine | — | — | — | 2.0 | — | — |
| lauryl betaine | — | — | — | — | 2.0 | — |
| cetyl betaine | — | — | — | — | — | 2.0 |
| water to 100% | → | → | → | → | → | → |
| pH 4.5 | → | → | → | → | → | → |

To compare the relative effectiveness of compositions of this invention containing a betaine and one which contains the cationic polymer and amphoteric surfactant but no betaine, the compositions of Examples 1 and 5, both without the betaine were prepared. In addition the following hair dye preparation was formulated to be applied before the hair conditioning treatment:

COMPOSITION A

| Ingredient | % by Wt. |
|---|---|
| p-phenylenediamine | 0.35 |
| N,N—bis(2-hydroxyethyl-p-phenylenediamine sulfate | 0.18 |
| resorcinol | 0.31 |
| 1-naphthol | 0.08 |
| oleic acid | 7.50 |
| propylene glycol | 4.40 |
| isopropanol | 4.35 |
| hydrogen peroxide | 3.00 |
| octoxynol-1 | 3.50 |
| sulfated castor oil | 1.50 |
| ammonium hydroxide | 1.15 |
| cocamide DEA | 0.75 |
| fragrance | 0.15 |
| sodium sulfite | 0.05 |
| EDTA | 0.01 |
| water QS to pH 9.8 | 100.00 |

Swatches of intact Caucasian hair were colored with Composition A above. This was applied to dry hair working the composition into a lather. The composition was permitted to remain in contact with the hair for 20 min. at ambient temperatures. A little warm water was then added to the hair and worked into a lather. The hair was then rinsed with water until the water ran clear. The ratio of the amount of solution to weight of hair, temperature and quantity of water used for rinsing after treatment, were all maitained to simulate conditions on the head. After rinsing, the conditioning materials of Example 1 with and without the betaine were applied to the dried hair (0.1 g of each product per 1 g of hair), and were worked in for 30 seconds and left on the hair for an additional 1 minute after which time the hair was rinsed and combed. The combing measurements were performed by the test described above by passing of a hair tress through a comb attached to a strain gauge which in turn is connected to a recording device. Work is expended to accomplish the passage of the hair tress through the comb, and this work, read off the integrator, is the objective measure of combing ease/difficulty.

Having determined the combing properties of hair after coloring and the subsequent comparative conditioning treatment, the swatches were shampooed with Herbal Essence shampoo the number of times indicated in Table I and again tested for combing. The shampooing procedure involved application of the shampoo (0.1 g per 1 g of hair), working it into the hair the rinsing the shampooed hair for at least 1 minute. Each shampoo step consisted of two lathering/rinsing sequences.

The results of combability tests are summarized in Table I below. In the Table, the "combing work" is expressed in units of work (gcm). The higher the values, the harder was it to comb the hair.

TABLE I

| | average combing work (gcm) on wet hair | | | | |
|---|---|---|---|---|---|
| Treatment With | Before Treatment | After Treatment | +4 Shampoos | +5 Shampoos | +6 Shampoos |
| Composition of Example 1 on hair dyed with the composition with betaine | 4,100 | 228 | 349 | 438 | 531 |
| Hair dyed and treated with the composition without betaine | 4,100 | 323 | 520 | 530 | 689 |

As will be noted, the hair treated with the composition of Example 1 of this invention containing the betaine is easier to comb both immediately after treatment as well as after several shampoos when compared with hair treated with the conditioning composition that does not contain the betaine. This result has been further confirmed in experiments on live heads.

A similar test was run comparing the results obtained with the aforesaid dyeing composition A by comparison of the composition of Example 5 with the same composition but omitting the betaine. The results obtained are summarized in Table II below.

TABLE II

| | average combing work (gcm) on wet hair | | | | |
|---|---|---|---|---|---|
| Treatment With | Before Treatment | After Treatment | +4 Shampoos | +5 Shampoos | +6 Shampoos |
| Composition of Example 5 on hair dyed with Composition A with betaine | 5,233 | 300 | 486 | 533 | 617 |

TABLE II-continued

| Treatment With | average combing work (gcm) on wet hair | | | |
|---|---|---|---|---|
| | Before Treatment | After Treatment | +4 Shampoos | +5 Shampoos | +6 Shampoos |
| Composition of Example 5 without betaine on hair dyed with Composition A | 5,233 | 580 | 641 | 809 | 916 |
| Composition of Example 5 on hair dyed with Composition A | 5,233 | 300 | 486 | 533 | 617 |
| Composition of Example 5 but without betaine on hair dyed with Composition A | 5,233 | 580 | 641 | 809 | 916 |

We claim:

1. A composition for the conditioning of hair treated with an alkaline medium prior to the conditioning, consisting essentially of, based on the total weight of the composition, from about 0.1% to about 10% of at least one cationic polymer product, from about 0.2% to about 20% of at least one amphoteric surfactant product, and sufficient acid to give the composition a pH in the range of from about 1 to about 6, wherein the ratio

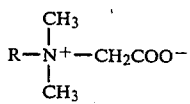

is from about 0.2 to about 5, in an aqueous carrier, and from about 0.1% to about 5.0% of at least one betaine of the formula:

$$R-\overset{CH_3}{\underset{CH_3}{N^+}}-CH_2COO^-$$

in which R is a long chain aliphatic radical containing 10 to 24 carbon atoms.

2. A composition according to claim 1 in which said ratio is in the range of from about 1 to about 2.

3. A composition according to claim 1 in which said betaine is cocamidopropyl betaine.

4. A composition according to claim 1 in which said betaine is lauryl betaine.

5. A composition according to claim 1 in which said betaine is oleyl betaine.

6. A composition according to claim 1 in which said betaine is cetyl betaine.

7. A composition according to claim 1 in which said betaine is coco betaine.

8. A composition according to claim 1 in which said cationic polymer product is at least one of a dimethyldiallylammonium chloride homopolymer, a polymeric quaternized dimethylbutenyl ammonium chloride terminated with quaternized triethanolamine groups quaternized poly-4-vinyl pyridine, or a quaternized poly-4-vinyl pyridine halide, poly(methacrylamidopropytrimethyl ammonium chloride), quaternized poly(vinylamine) and quaternized poly(ethyleneimine).

9. A composition according to claim 1 in which said cationic polymer product is quaternized poly-4-vinyl pyridine.

10. The composition of claim 9, wherein the anion is said QPVP is a halide, sulfate or carboxylate.

11. A composition according to claim 1 in which said cationic polymer product is a polymeric quaternized dimethylbutenyl ammonium chloride terminated with quaternized triethanolamine groups.

12. A composition according to any one of claims 2 to 11 or 1 wherein said amphoteric surfactant product is of the formula:

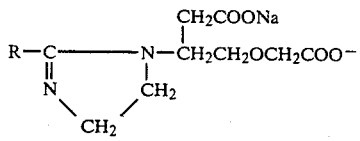

in which R is a long chain fatty radical containing 10 to 18 carbon atoms.

13. A composition according to any one of claims 2 to 11 or 1 in which said amphoteric surfactant product is of the formula:

$$R-NH-CHH_2-CH_2-COOH$$

in which R is a long chain fatty alkyl radical having from 10 to 18 carbon atoms.

14. In a process for conditioning hair which has been previously subjected to the treatment with a treating agent having an alkaline pH, the improvement which comprises applying to said pre-heated hair a compostion as defined in any of the claims 1 to 11 for sufficient time to improve its combing characteristics and/or its manageability, and/or its softness.

15. A process according to claim 14 in which the pH of said previous employed treating agent is in the range of from about 7 to 12.

16. A process according to claim 14 in which the pH of the said previous employed treating agent is in the range of from about 8 to 11.

* * * * *